(12) United States Patent
Winter, V et al.

(10) Patent No.: US 12,090,067 B2
(45) Date of Patent: Sep. 17, 2024

(54) METHOD FOR DESIGN AND MANUFACTURE OF COMPLIANT PROSTHETIC FOOT

(71) Applicant: Massachusetts Institute of Technology, Cambridge, MA (US)

(72) Inventors: Amos Greene Winter, V, Carlisle, MA (US); Kathryn Michelle Olesnavage, Ferndale, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/305,005

(22) Filed: Apr. 21, 2023

(65) Prior Publication Data

US 2023/0255800 A1  Aug. 17, 2023

Related U.S. Application Data

(63) Continuation of application No. 16/616,686, filed as application No. PCT/US2018/034628 on May 25, 2018, now Pat. No. 11,666,461.

(Continued)

(51) Int. Cl.
*A61F 2/50* (2006.01)
*B33Y 50/00* (2015.01)
(Continued)

(52) U.S. Cl.
CPC ............ *A61F 2/5046* (2013.01); *B33Y 50/00* (2014.12); *B33Y 80/00* (2014.12);
(Continued)

(58) Field of Classification Search
CPC .............. A61F 2/5046; A61F 2002/505; A61F 2002/6657; B33Y 50/00; B33Y 80/00; G05B 19/4099; G05B 2219/49023
See application file for complete search history.

(56) References Cited

U.S. PATENT DOCUMENTS

| 4,959,073 A | 9/1990 | Merlette |
| 5,219,365 A * | 6/1993 | Sabolich ................... A61F 2/66 623/53 |

(Continued)

FOREIGN PATENT DOCUMENTS

| DE | 102019100584 A1 | 7/2020 |
| WO | 2018/218139 A1 | 11/2018 |
| WO | 2020/247052 A1 | 12/2020 |

OTHER PUBLICATIONS

Olesnavage Kathryn M et al: "Lower Leg Trajectory Error: A novel optimization parameter for designing passive prosthetic feet", 2015 IEEE International Conference on Rehabilitation Robotics (ICORR), IEEE, Aug. 11, 2015.*

(Continued)

*Primary Examiner* — Thomas C Lee
*Assistant Examiner* — Ameir Myers
(74) *Attorney, Agent, or Firm* — Hamilton, Brook, Smith & Reynolds, P.C.

(57) ABSTRACT

A compliant prosthetic foot is designed and fabricated by combining a compliant mechanism optimization technique with a calculation of low leg trajectory error under a reference loading condition. The compliant mechanism optimization technique includes a set of determinants for the compliant prosthetic foot. An optimized set of determinants of the compliant prosthetic foot is formed that minimizes the (Continued)

lower leg trajectory error relative to a target kinematic data set. The compliant prosthetic foot is then fabricated in conformance with the optimized set of determinants.

21 Claims, 12 Drawing Sheets

Related U.S. Application Data

(60) Provisional application No. 62/511,467, filed on May 26, 2017.

(51) Int. Cl.
 *B33Y 80/00* (2015.01)
 *G05B 19/4099* (2006.01)
 *A61F 2/66* (2006.01)

(52) U.S. Cl.
 CPC .... *G05B 19/4099* (2013.01); *A61F 2002/505* (2013.01); *A61F 2002/6657* (2013.01); *G05B 2219/49023* (2013.01)

(56) References Cited

U.S. PATENT DOCUMENTS

| | | | |
|---|---|---|---|
| 6,254,643 B1* | 7/2001 | Phillips | A61F 2/66 623/55 |
| 8,423,167 B2* | 4/2013 | Sanders | G06F 30/00 700/118 |
| 9,486,334 B2* | 11/2016 | Tompkins | A61B 5/1123 |
| 10,478,121 B2* | 11/2019 | Pusch | A61B 5/1121 |
| 11,026,814 B2* | 6/2021 | Klute | A61F 2/66 |
| 11,607,325 B2 | 3/2023 | Winter et al. | |
| 11,666,461 B2 | 6/2023 | Winter et al. | |
| 2005/0187640 A1* | 8/2005 | Christensen | A61F 2/66 623/55 |
| 2005/0273179 A1 | 12/2005 | Townsend et al. | |
| 2007/0021858 A1* | 1/2007 | Slemker | A61F 2/5046 700/118 |
| 2010/0030343 A1* | 2/2010 | Hansen | A61F 2/6607 623/47 |
| 2011/0320012 A1 | 12/2011 | Christensen et al. | |
| 2016/0063139 A1* | 3/2016 | Cellier | F01D 9/041 703/1 |
| 2016/0206447 A1* | 7/2016 | Auberger | A61F 2/68 |
| 2017/0304082 A1 | 10/2017 | Lindhe | |
| 2018/0353308 A1* | 12/2018 | Tompkins | A61F 2/585 |
| 2019/0046335 A1 | 2/2019 | Adamczyk et al. | |
| 2020/0030121 A1* | 1/2020 | Mora Morales | A61F 2/66 |
| 2020/0085595 A1 | 3/2020 | Winter, V et al. | |
| 2020/0122403 A1* | 4/2020 | Dhokia | B29C 64/393 |
| 2020/0375763 A1 | 12/2020 | Winter et al. | |

OTHER PUBLICATIONS

A. Zhou, Shape and Size Synthesis of Compliant Mechanisms Using Wide Curve Theory, 2006, J. Mech. Des., vol. 128, No. 3, p. 551-558 (Year: 2006) (Year: 2006).*

Dung, Xu et al, "Freeform Skeletal Shape Optimization of Compliant Mechanisms", Journal of Mechanical Design, vol. 125, No. 2, Jun. 1, 2013, p. 253-261.

Filali, M.H., "Prothese du Pied en Materiaux Composites (Composite Material-Based Foot Prothesis)", Composites, Dlastiques Renforces Fibres de Verre Textile, Center Doc. Verre Textile Plas Re. Paris, FR, vol. 34, No. 2, Mar. 1, 1994, pp. 62-64.

Hong Zhou et al, "Shape and Size Synthesis of Compliant Mechanisms Using Wide Curve Theory", Journal of Mechanical Design, vol. 128, No. 3, May 1, 2006, p. 551.

Olesnavage, Kathryn M. et al., "Lower Leg Trajectory Error: A novel optimization parameter for designing paassive prosthetic feet", 2015 IEEE International Conference on Rehabilitation Robotics (ICORR), IEEE, Aug. 11, 2015, pp. 271-276.

European Patent Office, International Search Report and Written Opinion for PCT Application No. PCT/US2018/034628, Aug. 29, 2018, 14 pp.

Ossur, "Vari-Flex Catalog," Retrieved from Internet at: www.ossur.com (10 pages) dale unavailable.

International Preliminary Report on Patentability for Int'l Application No. PCT/US2018/034628, tilled: Method for Design and Manufacture of Compliant Prosthentic Foot, Issued: Nov. 26, 2019.

Winter, D.A., Biomechanics and Motor Control of Human Movement, John Wiley & Sons, 2009, Appendix A (pp. 1996-360).

Howell, LL, Compliant Mechanisms-John Wiley & Sons, 2001, pp. 1-3, 12-15, 301-329.

Lan, C.C. et al., "Distributed Shape Optimization of Compliant Mechanisms Using Intrinsic Functions"; Journal of Mechanical Design, vol. 130, Jul. 2008, 10 pp.

Hetrick, J. et al. "An Energy Formulation for Parametric Size and Shape Optimization of Compliant Mechanisms," Journal of Mechanical Design, vol. 121, Jun. 1999, pp. 229-234.

Zhou, H. et al., "Shape and Size Synthesis of Compliant Mechanisms Using Wide Curve Theory," Journal of Mechanical Design, vol. 128, May 2006, pp. 551-558.

International Preliminary Report on Patentability for Int'l Application No. PCT/US2020/026308, entitled "Shape Optimization for Prosthetic Feet," dated Dec. 7, 2021.

International Search Report and Written Opinion received for PCT Patent Application No. PCT/US2020/026308, entitles "Shape Optimization for Prosthetic Feet," mailed Oct. 26, 2020, 12 pages.

* cited by examiner

METHOD FOR DESIGN AND MANUFACTURE OF COMPLIANT PROSTHETIC FOOT

RELATED APPLICATION

This application is a continuation of U.S. application Ser. No. 16/616,686, which is the U.S. National Stage Application of International Application No. PCT/US2018/034628 filed on May 25, 2018, published in English, which claims the benefit of U.S. Provisional Application No. 62/511,467, filed on May 26, 2017. The entire teachings of the above applications are incorporated herein by reference.

BACKGROUND

Numerous studies have shown that the mechanical design of a passive prosthetic foot affects the users' gait. However, there is no consensus on exactly how the mechanical properties of a foot relate to the biomechanical performance. Without this relationship, it is impossible to optimize the design of a prosthetic foot for peak performance, or to evaluate potential tradeoffs when designing low cost feet for emerging markets with minimal sacrifice of performance.

However, the outputs of known topology optimizations generally several practical limitations; for example, they consist only of uniform elements or uniform cross-sections, have unclear boundaries or checkerboard patterns, or they result in localized flexural hinges with high stress concentrations. Moreover, the relationship between their mechanical properties and biomechanical functionality is not fully understood. One widely used metric is the roll-over geometry, which is defined as the path of the center of pressure during stance phase as measured in the ankle-knee reference frame. Roll-over geometry offers advantages over other metrics in that it can be evaluated for typical physiological walking, providing a target design shape, as well as mechanically for prosthetic feet without the inherent variability of human subjects. However, because roll-over geometry is measured in the ankle-knee reference frame without including any information regarding the orientation of the ankle-knee reference frame relative to the global reference frame, it is possible for two different prosthetic feet to have identical roll-over geometries but exhibit very different lower leg kinematics during gait. Therefore, roll-over geometry is insufficient as a design objective.

Other examples include three simple prosthetic foot architectures, each with two design variables: a rigid circular foot with the radius and horizontal position of the center of the circle as design variables, a foot with pin joints at the ankle and metatarsal with rotational stiffness of each joint as design variables, and a foot with a pin joint at the ankle and a compliant cantilever beam forefoot, with ankle stiffness and forefoot beam bending stiffness as design variables. While these architectures were quick to optimize, as the deformation in response to loads could be calculated analytically, the resulting prototypes are heavy, at 980 g after multiple design iterations intended to reduce weight, and complicated to manufacture, requiring pinned joints, springs, multiple fasteners, and bulky structural components.

Another method, called the Lower Leg Trajectory Error (LLTE), quantifies how closely the position of the lower leg segment for a given prosthetic foot is able to replicate target physiological lower leg positions throughout the course of a step. To-date, two degree-of-freedom architectures have effectively proven the concept of prosthetic foot optimization based on LLTE. However, such devices are generally large, heavy, and consist of relatively complex mechanisms.

Therefore, a need exists for a lighter, more robust, and easier-to-manufacture design.

SUMMARY

The invention generally is directed to a method for designing and manufacturing a compliant prosthetic foot with a calculation of lower leg trajectory error.

In one embodiment, the method includes combining a compliant mechanism optimization technique that includes a set of determinants for a compliant prosthetic foot with a calculation of lower leg trajectory error. An optimized set of determinants of the compliant prosthetic foot is formed that minimizes the lower leg trajectory error relative to a target kinematic data set. A compliant prosthetic foot is then fabricated that is in conformance with the optimized set of determinants.

This invention has many advantages. For example, the method of the invention results in a design for and fabrication of a single-part compliant foot that replicates typical lower leg kinematics, such as those of a human subject. The method is easily customizable to lower leg kinematics, body weight, and body size of an individual subject. The resulting compliant prosthetic foot generally has less mass and is simpler to manufacture than articulated ankle joints. The method can also be modified to incorporate additional design features, such as a heel component, and can be modeled on a variety of loading scenarios. The method of the invention can be employed to optimize a variety of loading scenarios, and to optimize the design of various portions of a prosthesis, such as the forefoot portion of a compliant foot prosthesis.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION OF THE INVENTION

Figure 1:
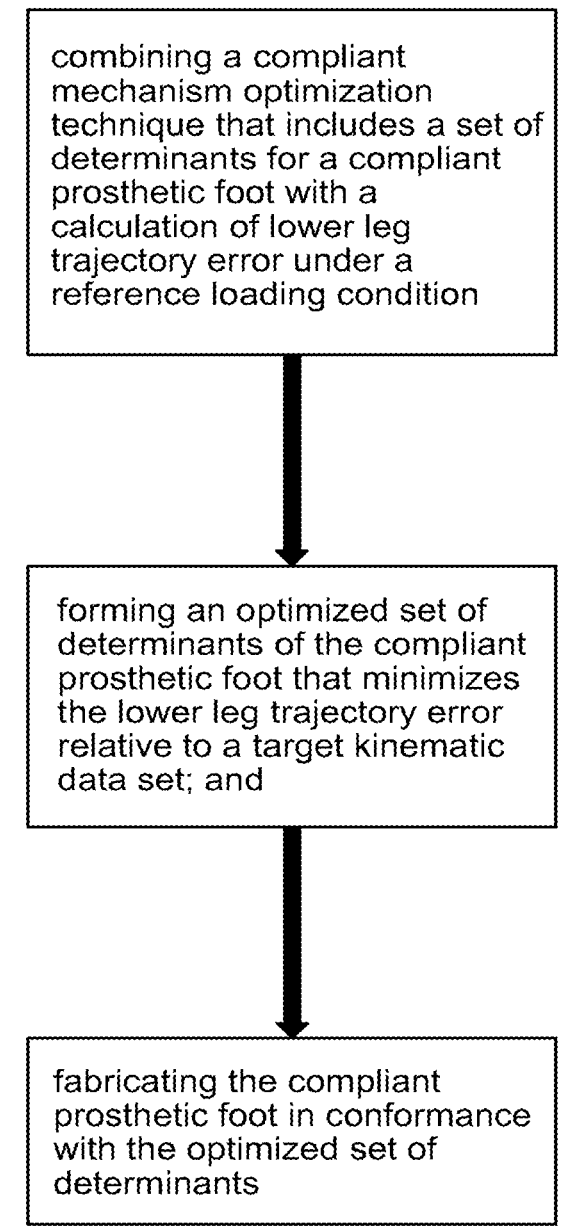
FIG. 1 is a schematic representation of one embodiment of the invention.

A description of example embodiments follows.

The invention generally is directed to a method for designing and manufacturing a compliant prosthetic foot.

In one embodiment, the invention is a method for fabricating a compliant prosthetic foot. The method in this embodiment includes the steps of combining a compliant mechanism optimization technique that includes a set of determinants for a compliant prosthetic foot with a calculation of lower leg trajectory error under a reference loading condition; forming an optimized set of determinants of the compliant prosthetic foot that minimizes the lower leg trajectory error relative to a target kinematic data set; and fabricating the compliant prosthetic foot in conformance with the optimized set of determinants. In one particular embodiment, the target kinematic data set includes a physiological data set. In another embodiment, the compliant mechanism optimization technique optimizes a set of determinants for a prosthetic foot that is compliant along its entire length. In another embodiment, the compliant mechanism optimization technique includes a parameterization step, wherein wide Bézier curve parameters are incorporated into a genetic algorithm to find a set of parameters that creates a foot that minimizes lower leg trajectory error. In still another embodiment, the compliant mechanism optimization technique employs a cubic curve defined by at least two control points. In another embodiment the cubic curve is defined by relative positions of four compliant points. In yet another embodiment, the compliant mechanism optimization technique employs a width from a Bézier curve as a variable, wherein the width is a function of control circles. In still another embodiment, the width of the Bézier curve is defined as a function of diameters of four control circles.

In another embodiment of the invention, the compliant mechanism optimization technique is combined with the lower trajectory error calculation by setting design parameters of the compliant prosthetic foot to not exceed a predefined design space. In one embodiment, the method further includes the step of setting the design parameters to limit the design of the compliant prosthetic foot to configurations that are realizable. In yet another embodiment, the set of determinants of the compliant prosthetic foot is set by finite element analysis. In one such embodiment, the finite element analysis includes setting time intervals within a gait cycle and conducting a finite element analysis for each time interval. In one such embodiment, the time intervals extend from foot flat. An example of such an embodiment includes employing a heel component in combination with the wide Bézier curve. In a particular embodiment, the time intervals extend from early stance plantar flexion. For example, in one embodiment, the target kinematic data set is a physiological data set obtained from a subject for whom a compliant prosthetic foot is being fabricated. In one embodiment, the target kinematic data set is a physiological data set obtained from an able-bodied subject with the same body size and mass as the subject for whom the component prosthetic foot is being fabricated. In another specific embodiment, the target kinematic data set is a physiological data set scaled from an able-bodied subject to adjust for differences in body size and mass compared to the subject for whom the compliant prosthetic foot is being fabricated. In another embodiment, the target kinematic data set is obtained by at least one member of the group consisting of: simulation, measurement of a subject, measurement of a population of subjects, and scaling a magnitude from at least one subject of a different body size and weight.

In yet another embodiment, the compliant prosthetic foot is fabricated by at least one method selected from the group consisting of: machining; three-dimensional printing; a layup method; a waterjet method; additive fabrication; subtractive fabrication; lamination; composite manufacture; injection molding; carbon fiber fabrication; extrusion; casting; molding; co-molding; carving; and vulcanization.

In yet another embodiment, the compliant prosthetic foot is fabricated of at least one member of the group consisting of: nylon 6/6; carbon fiber; fiberglass; spring steel; titanium; plastic; an alloy of metals; a polymer; a composite; a resin; a thermoplastic; a laminate; a rubber; an elastomer; a non-viscoelastic material; a viscoelastic material; and wood.

In an embodiment of the invention, shown schematically in FIG. 1, a compliant mechanism optimization technique that includes a set of determinants for a compliant prosthetic foot is combined with a calculation of lower leg trajectory error under a referenced loading condition. An optimized set of determinants of the compliant prosthetic foot is formed that minimizes lower leg trajectory error relative to a kinematic data set. A compliant foot is then fabricated in conformance with the optimized set of determinants.

As employed in the specification, "compliant mechanism optimization technique" is defined as a means of searching for, identifying, and designing a structure for a targeted deflection under a given load.

As employed herein, a genetic algorithm, or other optimization technique, may be used to determine the optimized set of determinants.

As employed herein, the term, "compliant prosthetic foot," is defined as a foot that deforms under load.

As employed herein, "reference loading condition," is defined as a targeted, anticipated, or targeted loading that the foot could experience.

As employed herein, "optimized set of determinants," is defined as the variables describing the size, form, shape, material, and structure of the foot in the configuration to provide a targeted deflection under a given load.

In one embodiment, the invention includes designing and optimizing prosthetic feet by replicating a target trajectory, e.g., the trajectory of the lower leg segment during physiological walking under typical ground reaction forces (GRFs). This approach is implemented by calculating the deformed shape of a given prosthetic foot under the GRFs at each instant during a step, using those deformed shapes to find the position of a lower leg segment at each time, then comparing those positions to the target kinematic data set using a root-mean-square error over the course of the step, a metric that is termed the Lower Leg Trajectory Error (LLTE). The optimal design is then the design that results in the minimum LLTE, that is, the design that best replicates the target kinematics, e.g., the physiological lower leg kinematics under the corresponding kinetics.

In one embodiment, design space parametrization, based on a wide Bézier curve, is employed, together with constraints to ensure only physically-meaningful shapes were considered. The LLTE value for a given design can be obtained by use of a suitable software, such as is known in the art. One example of suitable software is using MATLAB and ADINA finite element analysis (FEA) software.

Figure 2:
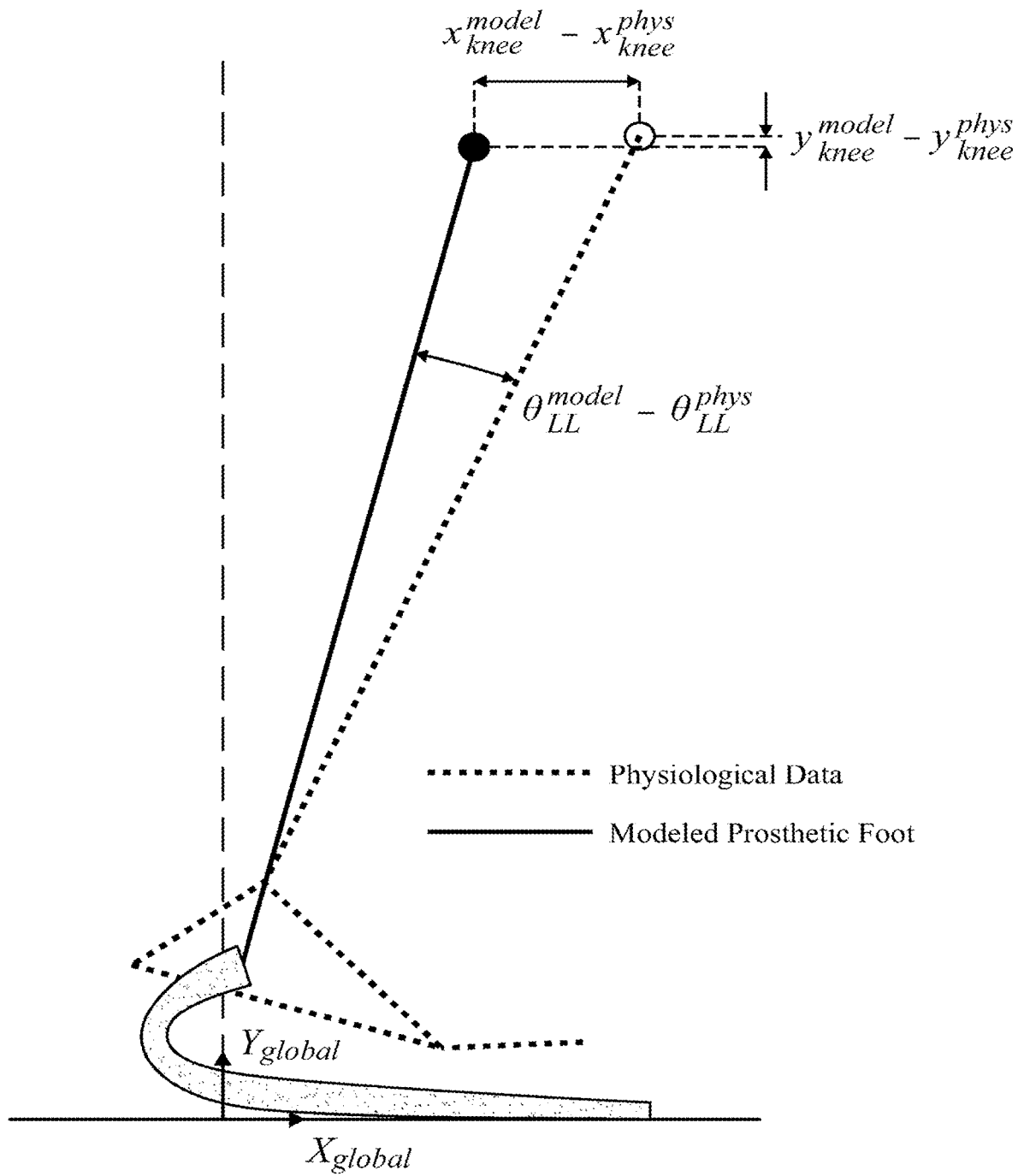
FIG. 2 is a schematic representation of variables of a lower leg trajectory error (LLTE) of a modeled prosthetic foot.

Lower Leg Trajectory Error (LLTE) is a metric that compares predicted kinematics for a lower leg to reference, or targeted, kinematics. LLTE can, in one embodiment, be defined as:

$$LLTE = \left[\frac{1}{N}\sum_{n=1}^{N}\left\{\left(\frac{x_{knee,n}^{model} - x_{knee,n}^{phys}}{\overline{x}_{knee}^{phys}}\right)^2 + \left(\frac{y_{knee,n}^{model} - y_{knee,n}^{phys}}{\overline{y}_{knee}^{phys}}\right)^2 + \left(\frac{\theta_{knee,n}^{model} - \theta_{knee,n}^{phys}}{\overline{\theta}_{knee}^{phys}}\right)^2\right\}\right]^{\frac{1}{2}} \quad (1)$$

where $x_{knee,n}^{model}$ and $y_{knee,n}^{model}$ are the horizontal and vertical positions of the knee and $\theta_{knee,n}^{model}$ is the orientation of the lower leg segment with respect to vertical, as calculated for a modeled prosthesis under an assumed set of ground reaction force and center of pressure data at the $n^{th}$ time interval, where stance phase is divided into a total of N intervals. The variables $x_{knee,n}^{phys}$, $y_{knee,n}^{phys}$ and $\theta_{LL,n}^{phys}$ refer to the same values as measured for target able-bodied walking, and $\overline{x}_{knee}^{phys}$, $\overline{y}_{knee}^{phys}$, and $\overline{\theta}_{LL}^{phys}$ are the mean physiological values over all N time intervals, which serve to normalize the errors in each variable. Each of these variables refers to the global, or lab-based, reference frame, as shown in FIG. 2, which shows the lower leg position for the modeled prosthetic foot (solid line) and target physiological gait data (dotted line) at one particular time interval during a step, with variables used in Eqn. (1) shown. Physiological data came from markers placed at anatomically relevant positions on a human subject, resulting in a gap between the marker positions and the ground (shown in FIG. 2). Physiological gait data employed by the method of the invention can be obtained from a suitable source, such as, for example, Winter's published data, which were obtained from a subject of body mass 56.7 kg and a length of 0.83 m Winter, D. A., 2009, Biomechanics and Motor Control of Human Movement, John Wiley & Sons, the relevant teachings of which are incorporated hereby by reference in their entirety (Winter's published gait data). Winter's published gait data is an example of a suitable physiological data set that is one embodiment of a suitable target kinematic data set, such as are known in the art. Alternative suitable target kinematic data sets include, those that include, for example, mobility data, stability data, energy reduction data, and comfort data.

The method of this invention includes designing and manufacturing a prosthetic foot structure having a single part that, in response to specific loading scenarios, deforms elastically in such a way as to achieve a desired output motion. In one embodiment, the foot formed by the method of the invention is a compliant foot. Suitable compliant mechanisms are known to those skilled in the art, such as, for example, are generally described in Howell, L. L., Compliant Mechanisms-John Wiley & Sons (2001), the relevant teachings of which are incorporated by reference in their entirety. In one embodiment, a suitable material at the ankle is attached to the rest of the prosthesis, which has a flat bottom surface at the prosthetic foot upon which the center of pressure can progress smoothly from heel-strike to toe-off. In this embodiment, the size and shape of the mechanism connecting the ankle to the bottom of the foot can be optimized.

Examples of known methods for compliant mechanism size and shape optimization techniques are described in Xu, D., and Ananthasuresh, G., 2003; "Freeform Skeletal Shape Optimization of Compliant Mechanisms", Transactions-American Society of Mechanical Engineers Journal of Mechanical Design, 125(2), pp. 253-261; Lan, C.-C., and Cheng, Y.-J., 2008; "Distributed Shape Optimization of Compliant Mechanisms Using Intrinsic Functions"; Journal of Mechanical Design, 130(7), p. 072304; Hetrick, J., and Kota, S., 1999; "An Energy Formulation for Parametric Size and Shape Optimization of Compliant Mechanisms," Ann Arbor, 1050, p. 48109; Zhou, H., and Ting, K.-L., 2006. "Shape and Size Synthesis of Compliant Mechanisms Using Wide Curve Theory," Journal of Mechanical Design, 128(3), pp. 551-558, the relevant teachings of which are incorporated by reference in their entirety.

In one embodiment, a wide Bézier curve, as presented by Zhou and Ting (Zhou, H., and Ting, K. L., 2006. "Shape and Size Synthesis of Compliant Mechanisms Using Wide Curve Theory," Journal of Mechanical Design, 128(3), pp. 551-558), is employed. Generally, a wide Bézier curve is a parametric curve with a shape dictated by a series of control points. With a Bézier curve, a cubic, or higher-order, curve can be defined by the positions of four control points, reducing a potentially complex shape to a limited number of design variables. The width is added as a variable by using control circles rather than control points and defining the width of the wide Bézier curve as a function of the diameters of these control circles. In one embodiment, the output of the optimization method employed is a 2D shape.

After the optimal keel design is determined, a flexural heel member can be added such that when a user of similar body mass to that for which the foot was designed places all of his or her weight at the end of the heel, an adequate factor of safety is retained (e.g. a safety factor of two).

The method of the invention yields a design that can be manufactured as, for example, a wide curve foot of a single nylon part fabricated by a suitable method, such as injection molding.

Figure 3:
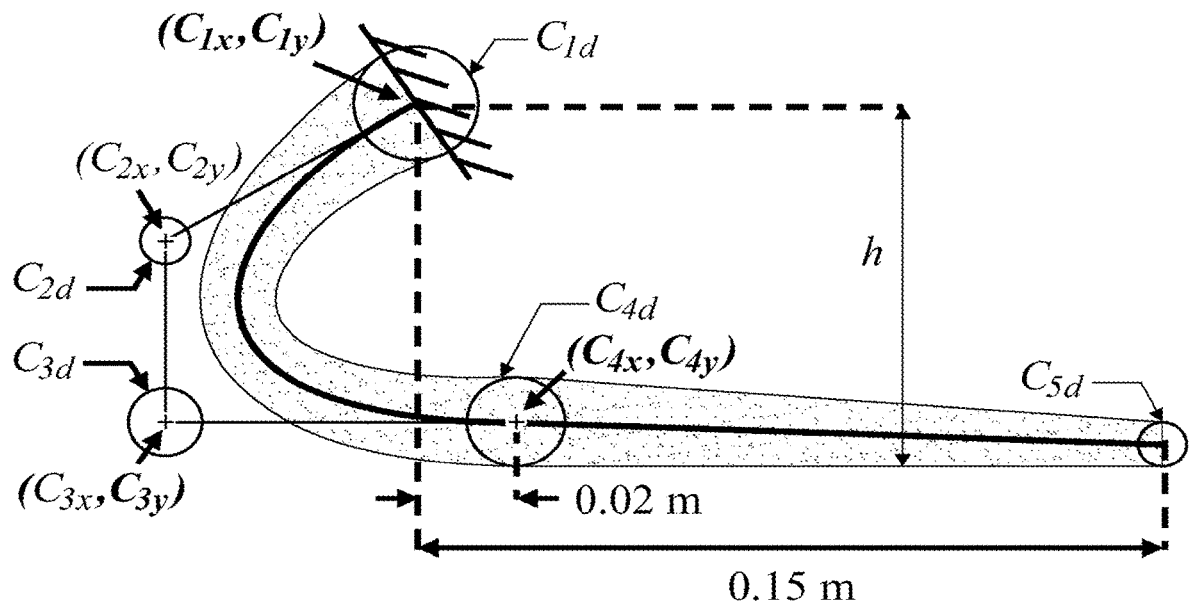
FIG. 3 is a representation of a parametrization of a keel of a foot wherein the shape and size of the keel are defined with nine independent design variables.

The complexity of the final design is limited by the definition of the design space, as is shown in FIG. 3. The heel can also be incorporated into the optimization rather than optimizing the keel and forefoot and then designing a heel around that structure. Loading scenarios from early stance plantarflexion, when the center of pressure is posterior to the ankle, can then be included in the LLTE evaluation. Similarly, the surface to which the male pyramid adapter is attached can be included to improve the accuracy of the boundary conditions on the finite element model.

The shape of the foot can be optimized, for example, based on five loading scenarios that are assumed to be adequately representative of the entire step. The lower leg trajectory of the prosthetic foot designed through the optimization can better replicate physiological gait kinematics throughout the whole step if more loading scenarios are included. The optimization runtime will scale linearly with the number of loading scenarios included, as each LLTE evaluation would perform an additional FEA simulation for each additional loading scenario, and the LLTE evaluation time is dominated by the FEA simulations. The number of function evaluations will not change significantly, so long as the rate of convergence is not affected by the number of loading scenarios. More or less than five loading scenarios can be employed in the method of the invention.

Input GRFs can be measured in the global reference frame, and then translated into the ankle-knee reference frame based on the orientation of the lower leg in the target, e.g., physiological data set to be applied to the ankle-knee reference frame-based FE model. The orientation of the ankle-knee reference frame of the wide Bézier curve foot during a particular load scenario depends on the deformed shape of the foot, which is dependent on the direction of the applied load. If the foot deforms in such a way as to exactly replicate the orientation of the ankle-knee reference frame in the physiological data set, that is, $\theta_{LL,n}^{model} - \theta_{LL,n}^{phys} = 0$ in Eqn (1), the loading in the FEA is exactly equivalent to that in the input physiological gait data when both are rotated back into the global reference frame. Otherwise, the GRF magnitude is equivalent, but it is rotated by an amount equal to $\theta_{LL,n}^{model} - \theta_{LL,n}^{phys}$ relative to the GRF as measured in the global reference frame. In one embodiment, the loading was rotated by a maximum of 4.18° relative to the direction of the GRF measured in the global reference frame. This source of error can be eliminated through iteratively solving for the orientation of the ankle-knee reference frame for the wide Bézier curve foot. This iterative process is repeated for each loading scenario, with each iteration requiring an additional FEA simulation until the orientation of the ankle-knee reference frame used to calculate the loads applied to the FE model converged with the ankle-knee reference frame found from the deformed shape of the foot. This consequently significantly increases the runtime of the LLTE evaluation for a single design, but does not affect the number of evaluations required for the optimization.

The optimal design generally is valid only for people of similar body mass and leg lengths as the subject with whom the data was recorded. The method can be applied using sets of gait data for various body masses and leg lengths to produce a range of prosthetic feet to accommodate a variety of potential users. Further, the input data can easily be adjusted proportionally to different users' body weight and size.

The flexibility of the LLTE-based design and optimization enable the creation of customized, 3D printed prosthetic feet for specific individuals.

The following is a demonstration of the invention, and is not to be considered limiting.

EXEMPLIFICATION

Method

Size and Shape Parameterization

A compliant prosthetic foot was designed and optimized. The compliant prosthetic foot structure consisted of a single part that, when acted upon by typical ground reaction forces, deformed in such a way as to best replicate typical lower leg kinematics, as quantified by minimizing the Lower Leg Trajectory Error (LLTE). By responding to a specific loading scenario and deforming elastically to achieve a desired output motion, the foot meets the definition of a compliant mechanism. Because the primary goal of this work was to develop a framework to produce an optimal prosthetic foot with minimal LLTE value, the design of the foot was kept as simple as possible for rapid implementation and iteration through the methodology. Therefore only the design of the forefoot was optimized, as many prosthetic feet decouple early stance from the rest of stance phase by using a separate mechanism, such as a cushion or a secondary compliant mechanism, for the heel portion of the foot. Several ways in which complexity could be added back into the design, including adding a heel in the optimization process, are discussed below. There is a plethora of literature on topology synthesis and optimization for compliant mechanisms, including continuum element density approaches, frame element based structures, and pseudo-rigid body models.

The shape and width of the Bezier curve (and resulting forefoot) was defined by five control points ($C_1$, $C_2$, $C_3$, $C_4$ and $C_5$ in FIG. 3), each of which had an x-position, y-position, and a diameter, denoted by subscripts x, y, and d, respectively. The first node, $C_1$, was the point of attachment between the foot and the rest of the prosthesis, and was fixed at $(C_{1x}; C_{1y}) = (0;0)$. Throughout the course of this work, all measurements and coordinates are in units of meters, unless otherwise stated. The height of the foot from the attachment point to the bottom of the foot was h, such that $$C_{4y} \equiv -h + \frac{1}{2}C_{4d},$$

where $C_{4d}$ was the width of the foot at $C_4$. To prevent any kinks in the structure, the tangent to the Bézier curve at point $C_4$ was made horizontal by enforcing $C_{3y} = C_{4y}$. The coordinate $C_{4x}$ was defined by the horizontal position of the center of pressure at the first instant in Winter's published gait data for which the center of pressure was anterior to the ankle in the ankle-knee reference frame, that is, $C_{4x} = 0.02$ m. The foot extended forward from $C_4$ to the tip of the foot, $C_5$, with $C_{5x} = 0.15$ m. Together, $C_{4x}$ and $C_{5x}$ determined the length of the forefoot and were selected to cover the distance the center of pressure progresses in Winter's gait data from foot flat to toe-off. The width of the forefoot decreased linearly from $C_4$ to the tip of the foot, with the design variable $ff_{frac}$ defining the ratio of the width of the tip of the forefoot to the width of the foot at $C_4$. That is, $ff_{frac} \equiv C_{5d}/C_{4d}$. In order to keep the foot flat and stable on the ground when it was unloaded, $C_{5y} = -h + \frac{1}{2} ff_{frac} \cdot C_{4d}$. Thus there were nine independent design variables to be optimized:

$$X = [h, C_{1d}, C_{2x}, C_{2y}, C_{2d}, C_{3x}, C_{3d}, C_{4d}, ff_{frac}] \quad (2)$$

Upper and lower bounds were imposed on each of the variables to constrain the shape and size of the structure to approximately fit within the envelope of a biological foot. The initial bounds were $$lb = [0.06, 0.005, -0.15, -0.10, 0.005, -0.15, 0.005, 0.005, 0.1] \quad (3)$$

and $$ub = [0.15, 0.04, 0.07, 0.10, 0.04, 0.01, 0.04, 0.04, 1] \quad (4)$$

Figure 4:
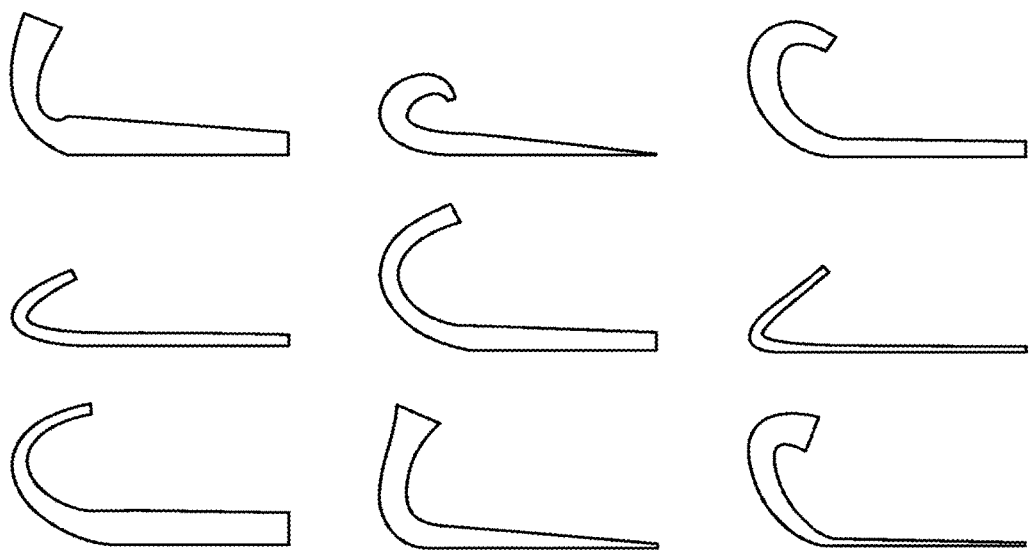
FIG. 4 is a representation of examples of various possible keel designs that can fall within a defined design space according to the method of the invention.

These preliminary bounds were very loose on the variables h, $C_{2x}$, $C_{2y}$, and $C_{3x}$ to avoid constraining the design space more than necessary. After an optimal design was found, these bounds were modified to enforce the requirement that the optimal design could not be larger than a biological foot. The thickness of the foot into the plane of the page was fixed at 0.06 m such that the foot can easily fit into a shoe or cosmesis. Examples of possible foot shapes explored through this particular parametrization are shown in FIG. 4.

Materials

The optimization was performed using nylon 6/6, with elastic modulus E=2.41 GPa and yield strength $\sigma_y$=82.7 MPa. Nylon was selected as a reasonable material choice for a low cost prosthetic foot because the high ratio of yield strength to elastic modulus allows nylon to achieve high deformations before yielding.

Constraints

Figure 5A:
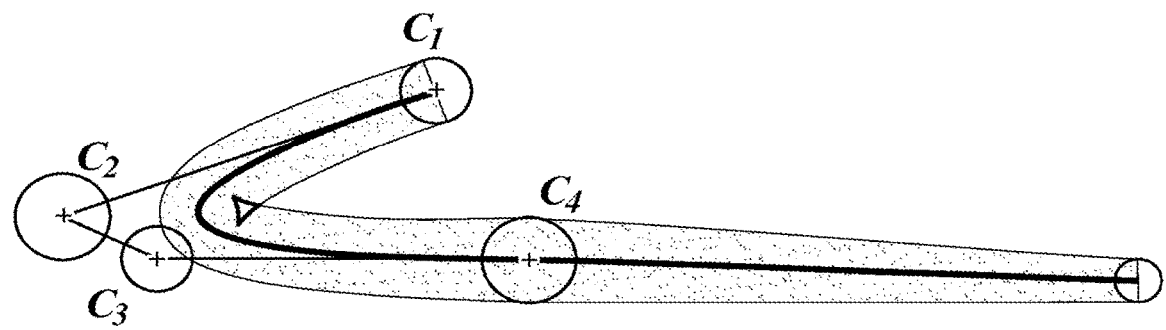
FIG. 5A is a representation of a self-intersection constraint violation excluded by an embodiment of a method of the invention.
Figure 5B:
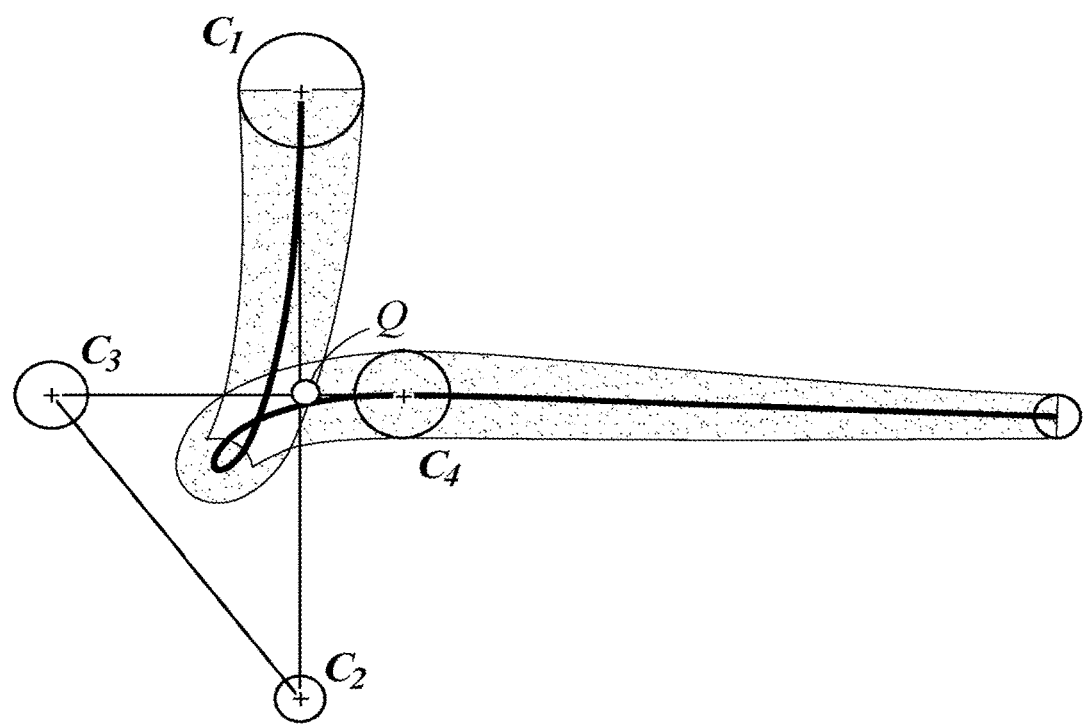
FIG. 5B is a representation of a loop constraint violation excluded by an embodiment of the invention.

Particular sets of design variables could yield wide Bézier curves that intersect themselves, resulting in a shape with no physical meaning. Self-intersection occurs either when the radius of curvature of the center Bézier curve is less than half the width of the outer shape (FIG. 5A), or the center curve creates a loop (FIG. 5B). These self-intersections can be prevented with the following constraints:

$$\max(0.5 w_c - \rho) \leq 0 \quad (5)$$

and $$\left( \frac{|\overline{C_1 C_2}|}{|\overline{QC_1}|} - \frac{4}{3} \right)\left( \frac{|\overline{C_2 C_3}|}{|\overline{QC_2}|} - \frac{4}{3} \right) - \frac{4}{9} \leq 0, \quad (6)$$

where $\rho$ is the radius of curvature of the center Bézier Curve, Q the point of intersection of line segments $\overline{C_1 C_2}$ and $\overline{C_3 C_4}$, as shown in FIG. 6B, and $|\overline{C_1 C_2}|$ is the length of the line segment between control points $C_1$ and $C_2$ and so on.

Since the size and shape parameterization defined $C_{3y} \equiv C_{4y}$ and the shape has been defined such that the bottom of the control circle $C_4$ is the bottom of the foot, if $C_{3d}$ were greater than $C_{4d}$ then the foot could protrude below the intended bottom surface. Therefore the linear inequality constraint $$C_{3d} - C_{4d} \leq 0 \quad (7)$$

was included.

Finally, a constraint was imposed to limit the maximum stress in the foot structure:

$$\sigma_{max} - \sigma_{allow} \leq 0, \quad (8)$$

where $\sigma_{allow} \equiv \sigma_y / F.S.$ with F.S., the factor of safety, equal to 2 in this case. The maximum stress in the structure, $\sigma_{max}$, was found through finite element analysis.

Evaluating LLTE

For simple foot architectures, the deformation of the foot under a given load can be calculated analytically. Thus each, $x_{knee,n}^{model}$, $y_{knee,n}^{model}$, and $\theta_{knee,n}^{model}$ calculation in Eqn. (1) was computationally inexpensive, so it was possible to find these values for every time interval during a step for which data were available. Using Winter's published data set and only considering the portion of stance for which the ankle angle is less than 90°, there are data for a total of N=26 time intervals.

Figure 6:
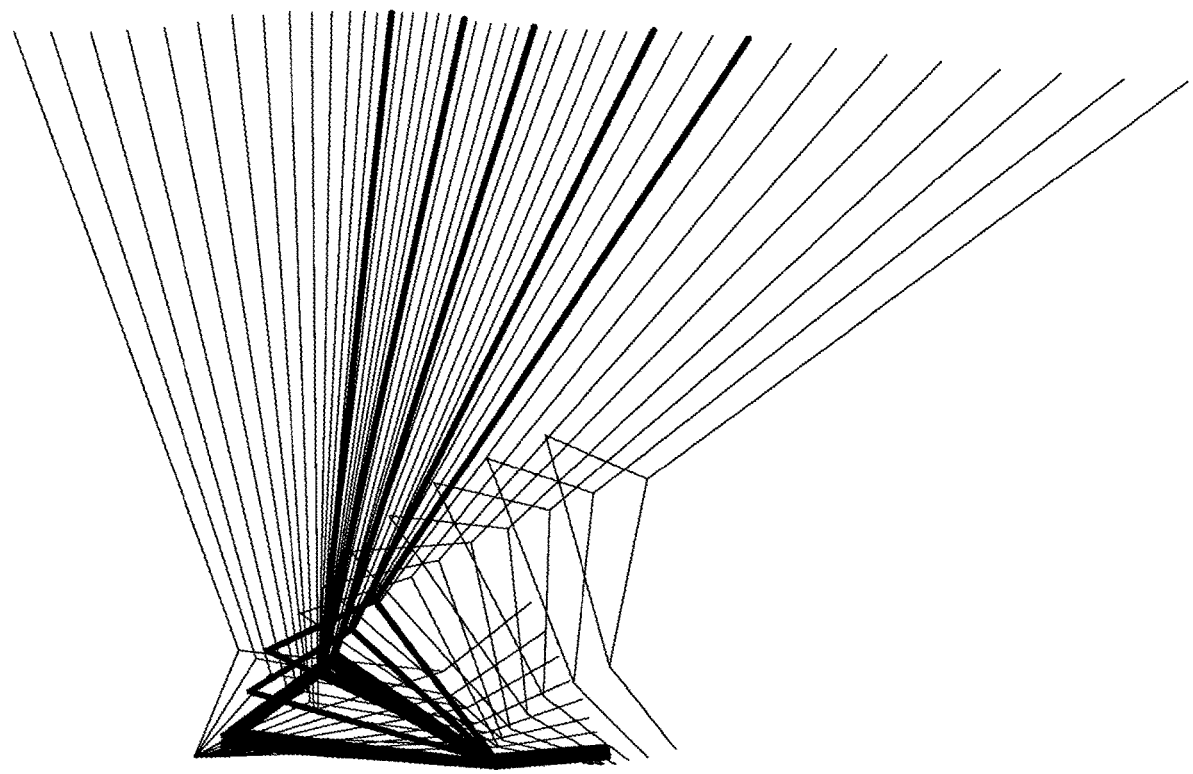
FIG. 6 is a representation of time intervals during stance included in gait data of a subject and employed in an embodiment of the invention.
Figure 7A:
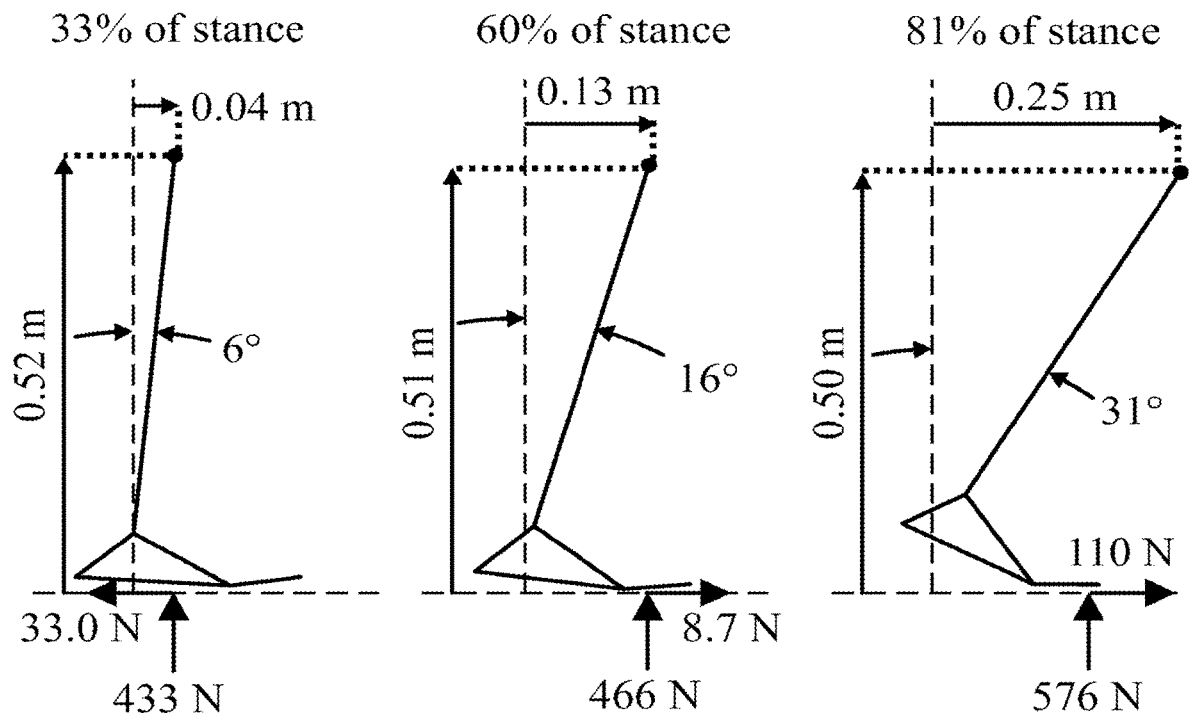
FIG. 7A is a representation of a global reference frame for a free body diagram of ground reaction forces on feet and lower leg position during three of five time intervals employed in a finite element lower leg trajectory error calculation according to one embodiment of the method of the invention.
Figure 7B:
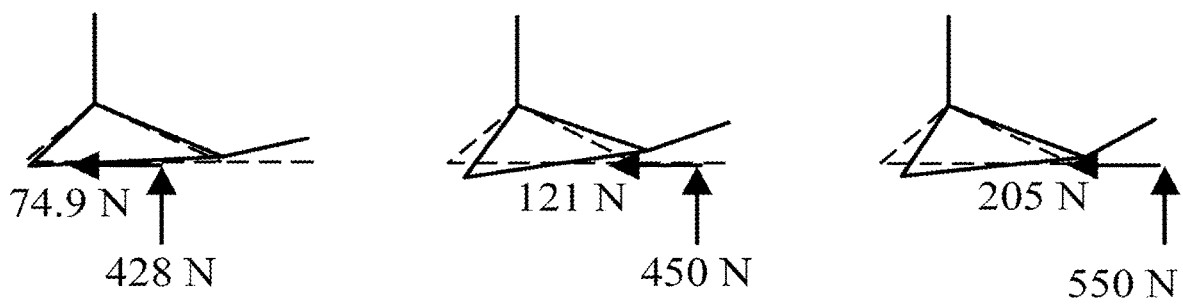
FIG. 7B is a representation of an ankle-knee reference frame for a free body diagram of ground reaction forces on feet and lower leg position during three of five time intervals employed in a finite element lower leg trajectory error calculation according to one embodiment of the method of the invention.

For the shapes of prosthetic feet considered in this work, there is no analytical solution to find the deformation of the foot structure in response to a given load. Rather, finite element analysis is required. To evaluate the LLTE for a single design, FEA must be performed N times to calculate the deformation at each of the N time intervals. Since FEA is computationally expensive, it is advantageous to minimize the number of time intervals required. To determine how many time intervals were necessary and which instances during the step best represented the step as a whole, the LLTE optimization was performed for simple analytical prosthetic foot models using each possible subset of the 26 total data points. It was found that with N=5, the optimal design variable values were each within 5% of those values found using all 26 data points if the five data points used were at 33%, 48%, 60%, 74%, and 81% of stance, where 0% is heel strike, 24% is the instant at which the ankle begins to dorsiflex past a neutral position, and 100% is toe-off (FIG. 6). As an example of the data used as model inputs and target outputs, the ground reaction forces and the positions of the lower leg segment for three of these five time intervals from Winter's data are shown in FIGS. 7A and 7B. For a given foot design, FEA was performed on the foot five times, once for each of the five time intervals.

The x, y, and $\ominus$ coordinates of the knee and lower leg segment can be found from just the position of the node at which the GRFs were applied, given by $(x_{load}, y_{load})$ and the position of a node at the tip of the foot, $(x_{end}, y_{end})$, where each of those positions refer to the deformed foot under loading. For the purposes of this calculation, the end node to which $(x_{end}, y_{end})$ refers was a virtual point added to the FEA model at a position of 20 cm anterior to the ankle. This was 5 cm beyond the end of the physical foot, but provided a useful point that could be used to calculate the angle of the ground relative to the foot in the ankle-knee reference frame, particularly when the center of pressure was very close to the tip of the physical foot. Because the toe of the foot was unconstrained and the only external loads were the ground reaction forces, there were no internal bending moments within the foot structure between the point at which the GRFs are applied and the tip of the finite element model of the foot. Consequently, this portion of the foot is undeformed, and the bottom of the foot distal to the loading point remains straight. For the center of pressure between the foot and the ground to indeed be at the node at which the loads have been applied, this entire segment of the foot, between the load point and the end of the foot, must be flat on the ground. The virtual end point on the finite element model does not affect these results; it only makes the length of the segment in contact with the ground longer, making the calculation of the angle of that segment more accurate. This is true as long as the center of pressure is proximal to the very end of the physical foot. When the center of pressure is at the end of the foot, the foot is only in point contact with the ground and can rotate rigidly about that point, so the position of the prosthesis is underconstrained by just the ground reaction forces and center of pressure and cannot be calculated from the ground reaction forces and center of pressure position without additional assumptions. Thus only the portion of stance right up until the center of pressure reaches this point is included in the optimization.

Figure 8:
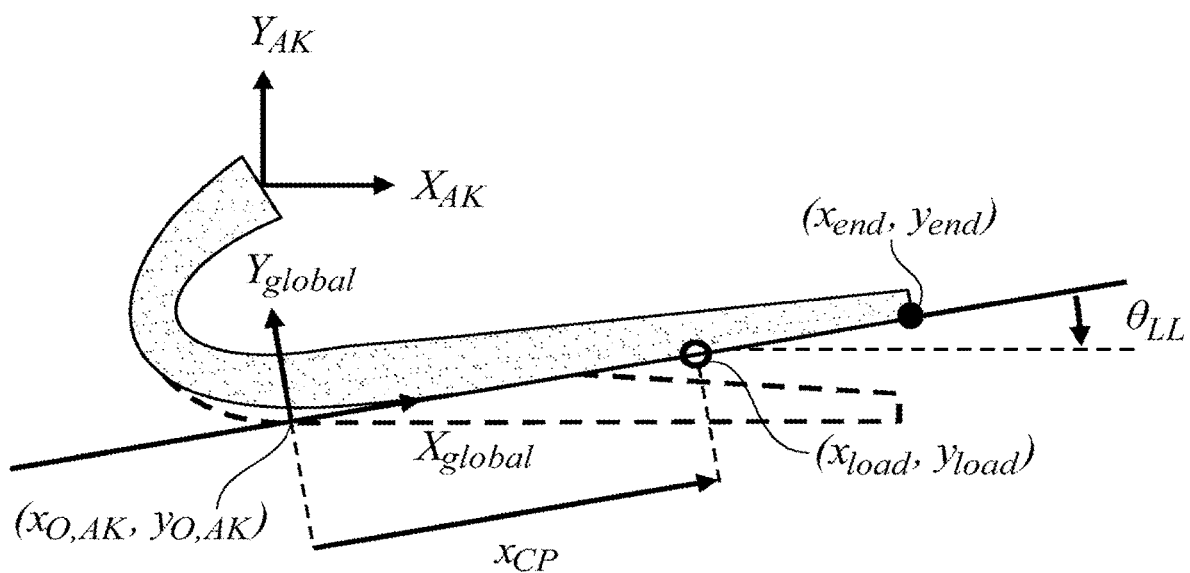
FIG. 8 is a representation of a deformed foot resulting from a finite element (FE) model in an ankle-knee reference frame with the variables employed in equations (9)-(11) labeled.

The angle between the ground and the horizontal in the ankle-knee reference frame in which the FEA was performed, and, equivalently, the angle of the lower leg segment with respect to vertical in the global reference frame, was calculated from the FEA results as $$\theta_{LL} = \tan^{-1}\left(\frac{y_{end} - y_{laod}}{x_{end} - x_{load}}\right), \quad (9)$$

as shown in FIG. 8. The variables $X_A K$, $Y_{AK}$, $X_{global}$, and $Y_{global}$ of FIG. 8 denote the x- and y-axes of the ankle-knee reference frame and the global reference frame, respectively. FIG. 8 is an example of a deformed foot result from the FE model in the ankle-knee reference frame with the variables used in Eqns. (9)-(11) labeled.

In the global reference frame, the origin was defined as the point of intersection between the ankle-knee axis and the ground when the ankle-knee axis is perpendicular to the ground during stance. Because the center of pressure data used as an input to the model is measured in the global reference frame, the x-coordinate of the center of pressure in the global reference frame is the distance between the center of pressure and the origin of the global reference frame along the ground. Then the coordinates of the global origin in the ankle-knee reference frame, $x_{O;AK}$ and $Y_{O;AK}$ are given by $$\begin{bmatrix} x_{O,AK} \\ y_{O,AK} \end{bmatrix} = \begin{bmatrix} x_{laod} - x_{cp}\cos\theta_{LL} \\ y_{laod} - x_{cp}\sin\theta_{LL} \end{bmatrix}. \quad (10)$$

Figure 9:
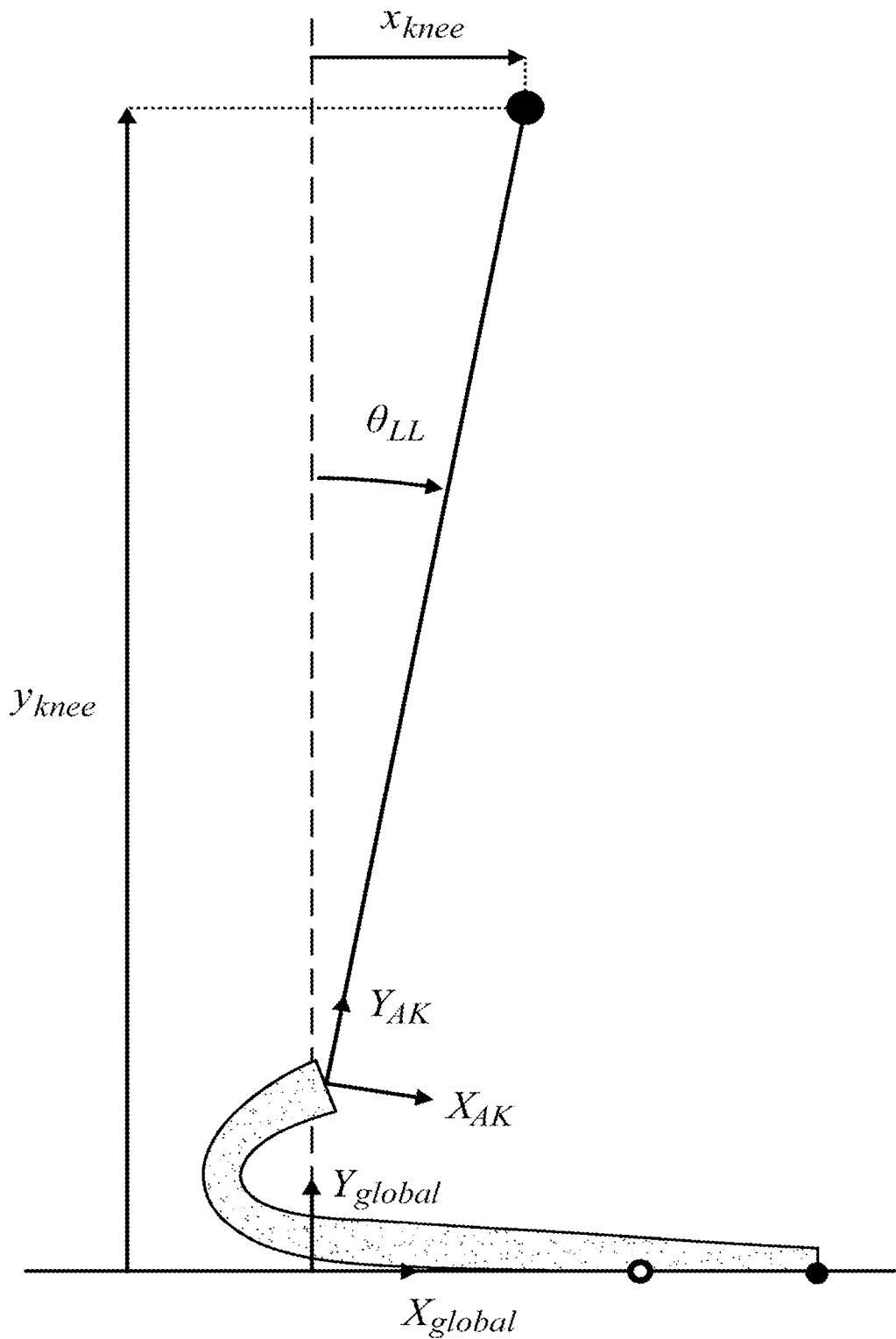
FIG. 9 is a schematic representation of a deformed foot finite element modeling results obtained from FIG. 8 rotated into the global reference frame.

Finally, the position of the knee in the global reference frame was found by taking the vector from the global reference frame origin to the knee in the global reference frame, then rotating the vector by $\Theta_{LL}$ (FIG. 9). That is, $$\begin{bmatrix} x_{knee} \\ y_{knee} \end{bmatrix} = \begin{bmatrix} \cos\theta_{LL} & \sin\theta_{LL} \\ -\sin\theta_{LL} & \cos\theta_{LL} \end{bmatrix} \cdot \begin{bmatrix} x_{AK} - x_{O,AK} \\ y_{AK} - y_{O,AK} \end{bmatrix}, \quad (11)$$

where $x_{AK}$ and $y_{AK}$ are the coordinates of the knee in the ankle-knee reference frame, so $x_{AK}=0$ and $y_{AK}=L_{AK}$, with $L_{AK}$ the length of the shank between the ankle and the knee, which is the distance from the knee to the ground in the input physiological data set minus the height of the prosthetic foot, h, for the particular design in consideration.

To automate the LLTE calculation for a particular design to allow for optimization, a custom MATLAB script was used to write and save text files containing input batch commands for ADINA, the commercially available FEA software used in this optimization. The commands within the text files defined the foot geometry as a 2D plane stress solid, meshed the surfaces using nine-node elements with edge length 2 mm, defined the material properties, and applied the appropriate loads. The displacement and strain options for the solver were left to their default value, which allows the solver to determine whether large or small displacement and strain formulations are more appropriate. A boundary condition was applied at the ankle to fix all degrees of freedom, as the analysis was performed in the ankle-knee reference frame, so any external loads would be opposed by reaction forces and moments at the ankle point, where the prosthetic foot would connect to the rest of the prosthesis. The finite element analysis was run via command line prompts executed through MATLAB. The results, namely the deformed position of the load node and the end node, were saved in another text file, which was read and processed via another custom MATLAB script, which calculated the $x_{knee,n}^{model}$, $y_{knee,n}^{model}$, and $\theta_{LL,n}^{model}$ corresponding to that load case using Eqns. (9)-(11). This was repeated for the other four load cases. Finally, the $x_{knee,n}^{model}$, $y_{knee,n}^{model}$, and $\theta_{LL,n}^{model}$ n and the target physiological $x_{knee,n}^{phys}$, $y_{knee,n}^{phys}$, and $\theta_{LL,n}^{phys}$ values for all five cases were used with Eqn. (1) to calculate the LLTE value for that set of design variables. The variables $X_{knee}$, $Y_{knee}$ and $\Theta_{knee}$ were input to Eqn.(1) to compare these resulting kinematics to the target physiological data.

Optimization Problem Formulation

The following optimization problem was solved to design the foot.

$$\left. \begin{aligned} &\min_{x}: LLTE(X) \\ &\text{subject to: } \max(0, 5w_c - \rho) \le 0 \\ &: \left(\frac{\overline{IC_1C_2}}{\overline{IQC_1}} - \frac{4}{3}\right)\left(\frac{\overline{IC_2C_3}}{\overline{IQC_2}} - \frac{4}{3}\right) - \frac{4}{9} \le 0 \\ &: C_{3d} - C_{4d} \le 0 \\ &: \sigma_{max} - \sigma_{allow} \le 0 \end{aligned} \right\} \quad (12)$$

The optimization was performed using a hybrid of MATLAB's built-in genetic algorithm function and pattern search optimization function. The objective function was a custom script which returned the LLTE value of a particular design following the previously described method. A custom mutation function was used in the genetic algorithm to increase the likelihood of valid mutations within the design variable bounds. The default mutation function in MATLAB for a bounded problem attempts a single random mutation without regards to bounds, then only uses this mutation in the next generation if all bounds happen to be met. If any one of the design variables is outside of its bounds, the mutation is not used. The original design is passed on to the next generation unchanged. This results in premature convergence on local minima. The custom mutation function changed each variable individually by a random amount selected from a normal distribution, similar to the default MATLAB mutation function for unbounded optimization problems. To account for the bounds, the standard deviation for one side of the normal distribution was decreased when a design variable was very close to one of its bounds such that it was unlikely that a mutated design variable would exceed the bound. If it did exceed the bound, that design variable was set equal to the bound it exceeded in the following generation.

This mutation function increased the diversity of designs explored through the genetic algorithm, increasing the likelihood that the optimal design found by the algorithm was indeed the global minimum. To further ensure this was the case, the optimization was repeated five times to check that each of the optimal designs returned were nearly identical.

Prototype Fabrication and Finite Element Model Validation

Once the optimal keel design was found, a heel and a surface to attach the ankle of the foot to the rest of the prosthesis were incorporated. The heel was designed to be as thin as possible while maintaining a minimum factor of safety of two on the structure so that the bending of the heel beam would mimic early stance plantarflexion. The thickness of the heel beam was approximated by analytically calculating the thickness that would result in a factor of safety of two at the base of the heel beam. A heel beam of the calculated thickness was then added to the finite element model of the foot. The maximum heel strike ground reaction force from Winter's gait data was applied to the finite element model, and the resulting stress calculated. The thickness of the heel beam was adjusted until the minimum factor of safety in the structure was approximately equal to two.

The ankle of the finite element model foot used in the optimization was rigidly fixed to the rest of the prosthetic leg. To best replicate this condition without increasing the height of the foot more than necessary, material was added to the ankle portion of the foot, creating a horizontal surface to which a male pyramid adapter, the standard attachment method for prosthetic components, could be affixed.

Finally, the toe and heel of the foot were rounded. According to subjects, the rounded heel and toe allow for smoother transitioning to and from the prosthetic foot, as well as improved maneuverability. The vertical thickness of the foot was adjusted to maintain the same bending stiffness in the toe despite the change in width into the plane of the page (from the reference of looking at the profile of the foot).

Figure 10:
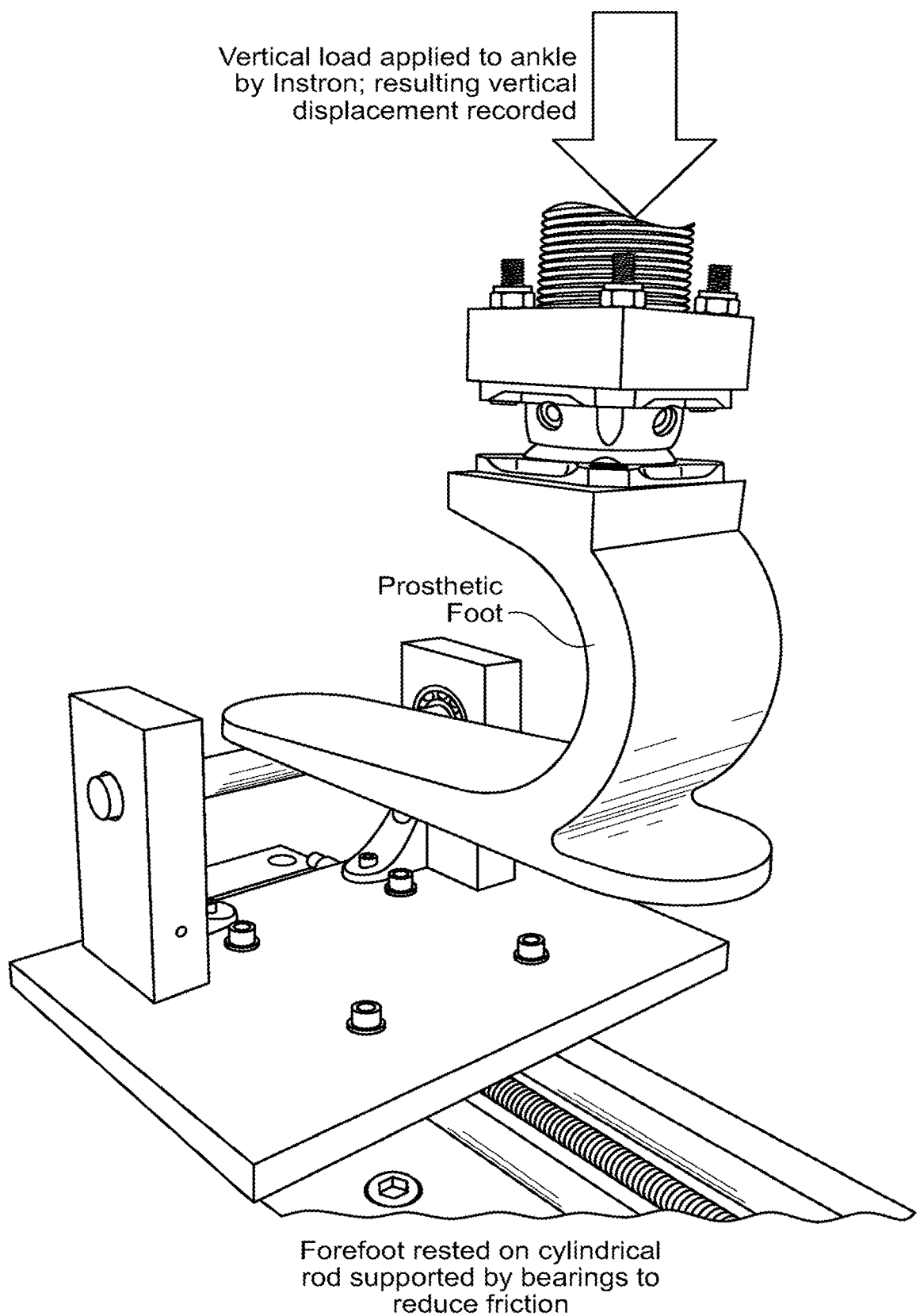
FIG. 10 is a perspective view of an experimental setup employed to measure vertical displacement of the forefoot in response to applied vertical loading up to 658 N to validate a finite element model of a foot.

The prototype was machined from nylon 6/6 and a male pyramid adapter was attached to the ankle. An Instron material testing machine was used to measure the displacement of the prosthetic foot in response to loading and verify that the finite element analysis accurately modeled the prosthetic foot. To constrain the position of the load acting on the foot, the forefoot was placed on a cylindrical rod mounted on rotational bearings in a jig rigidly affixed to the lab bench (FIG. 10). This setup ensured the contact load on the forefoot would be normal to the face of the rod. The vertical load applied by the Instron was increased from 0 N to 658 N. At regular intervals during loading, the vertical displacement and the angle of the forefoot relative to the fixed circular rod were measured and recorded. The forefoot angle was used to calculate the horizontal load acting on the foot, as the Instron controls and records only vertical loads.

The measured vertical loads and calculated horizontal loads at seven different instances throughout loading were applied to the finite element model of the foot, including the heel and ankle attachment surface. A fully fixed boundary condition was applied to the surface of the ankle to which the male pyramid adapter was attached. The vertical displacement of the load point in response to these loads was computed and compared to the equivalent value measured during Instron testing.

Preliminary Testing

Prototype prosthetic feet were employed in qualitative testing at Bhagwan Mahaveer Viklang Sahayata Samiti (BMVSS) an organization in Jaipur, India, to determine whether there were any obvious shortcomings of the methodology or this particular foot that needed to be addressed before an extensive study could be performed to quantitatively evaluate the prosthetic foot. A total of six subjects with unilateral transtibial amputation, all of whom had at least one year of experience using a Jaipur Foot, were fit with the prototype. The subjects walked around a room with a smooth, tiled floor until they were comfortable with the prosthetic foot. They were then asked to go up and down stairs and ramps, then finally outside to walk on uneven surfaces. This testing lasted no more than one hour. After completing these activities, the subjects provided qualitative assessments of the prototype. Quantitative metrics, such as Lichert scales, were not used, as experience has shown that subjects at BMVSS, most of whom are illiterate and have little to no formal education, are unfamiliar with the concept of numerical ratings, even if the numbers are replaced by textual descriptions (e.g. very bad, bad, ok, good, very good, etc.). Consequently, results from such studies are unreliable and can be misleading. However, if asked to qualitatively compare a prototype foot to his or her own prosthetic foot, the subjects are able to provide insightful responses that are informative for future design iterations.

Results

Figure 11:
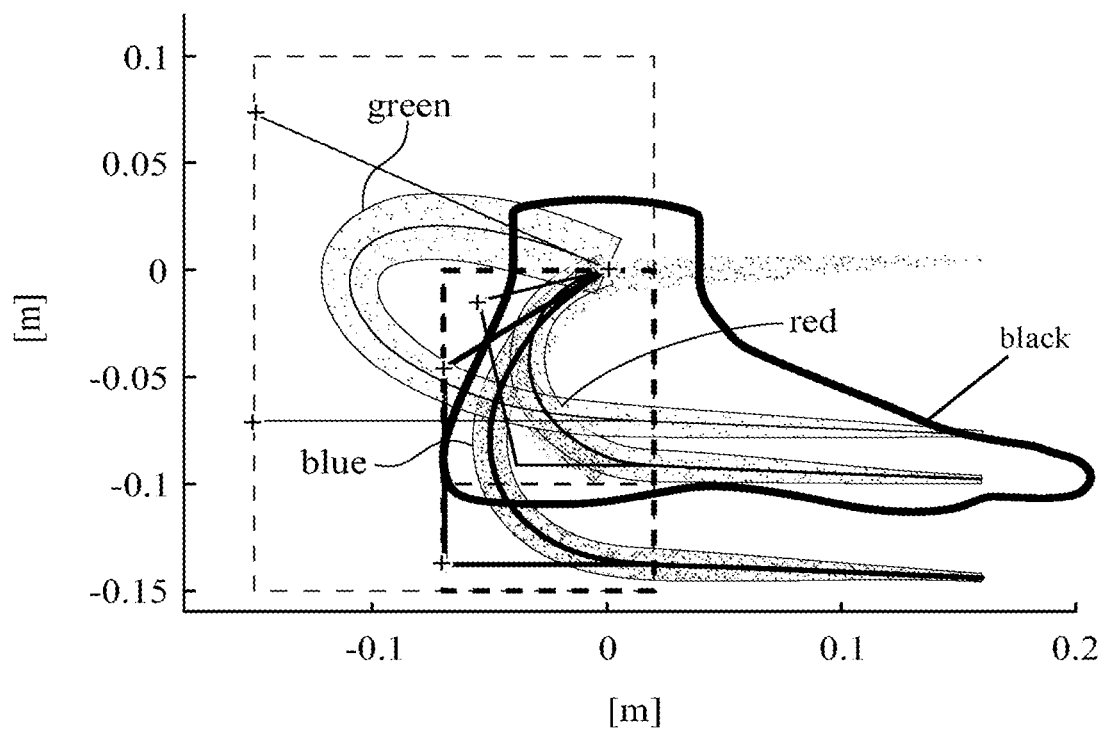
FIG. 11 is a representation of optimal keel designs found through the wide Bézier curve optimization method.

With the initial bounds given in Eqn. (3) and (4), the optimal design resulting from the optimization was $$X=[0.1461,0.0142,-0.0698,-0.0455,0.0202,-0.0690,0.0156,0.0170,0.1031]$$

with an LLTE value of 0.145. However, this design extended 12.2 cm posterior to the ankle, far too much to fit in a standard shoe (FIG. 11). The initial bounds resulted in a foot with an LLTE value of 0.145 ("green"), but too large to fit within the envelope of a biological foot (outlined in "black"). The subsequent designs, shown ("blue"), and finally in ("red"), have higher LLTE values, at 0.153 and 0.186, respectively, but only the final optimal design ("red") meets the size and shape requirements of a prosthetic foot that can be used in daily life. Note that in this figure, the three designs and the outline of the foot are aligned by the ankle position as defined above. The length of the pylon connecting the user's socket to the ankle of the foot would be adjusted to ensure the length of the prosthetic-side leg was equal to that of the biological leg.

Figure 14:
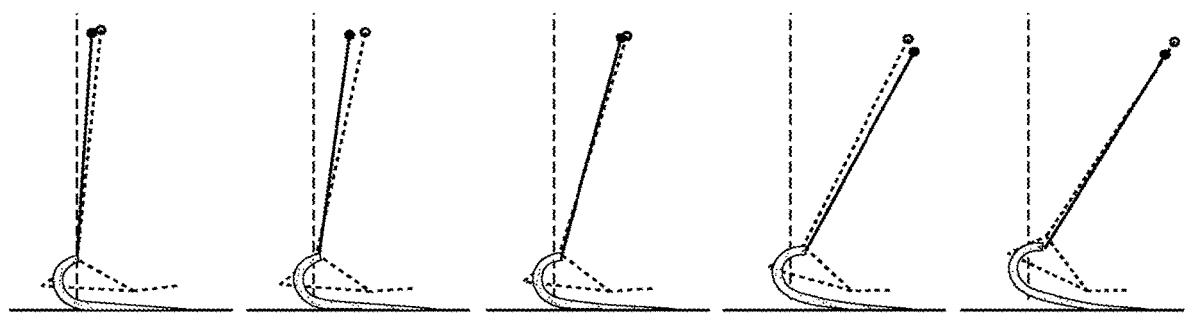
FIG. 14 is a lower leg trajectory for the final optimal foot (Bézier curve shown in FIG. 3, wherein the solid line shows lower leg trajectory) compared to the target physiological lower leg trajectory (dotted line) for each of the five loading scenarios considered. The physiological data shows the position of the markers at the knee, ankle, metatarsal, and toe as collected during typical, unimpaired walking. Because these markers were placed at physical locations on the subject's foot, there was space between the markers and the ground in the physiological data.

The lower bounds on $C_{2x}$ and $C_{3x}$ were then increased from −0.15 m to −0.07 m to limit the length of the foot in the posterior direction. Additionally, the upper bound on $C_{2y}$ was decreased from 0.10 m to 0.00 m to force the foot to not extend above the ankle, which would make attaching the foot to the rest of the prosthesis difficult. With these new bounds, the optimization was run again, yielding an optimal design of $$X=[0.1461,0.0142,-0.0698,-0.0455,0.0202,-0.0690,0.0156,0.0170,0.1031],$$

with an LLTE value of 0.153. The optimal design no longer extended too far posterior to the ankle, but was very tall, with the vertical distance from the bottom of the foot to the ankle, h, nearly 15 cm. This would preclude users with long residual limbs from using the foot. To obtain the final optimal result, the upper bound for h was decreased from 0.15 m to 0.10 m, producing an optimal design of $$X=[0.996,0.0142,-0.0556,-0.0139,9.0178,-0.0389,0.0160,0.0162,0.1034],$$

which had an LLTE value of 0.186 and fit completely within the envelope of a biological foot. The maximum stress in this final optimal design was 41.3 MPa, for a minimum factor of safety of 2.00. The position of the modeled lower leg segment for this final optimal design, as calculated using finite element analysis, is compared to the target physiological lower leg trajectory in FIG. 14.

Figure 12:
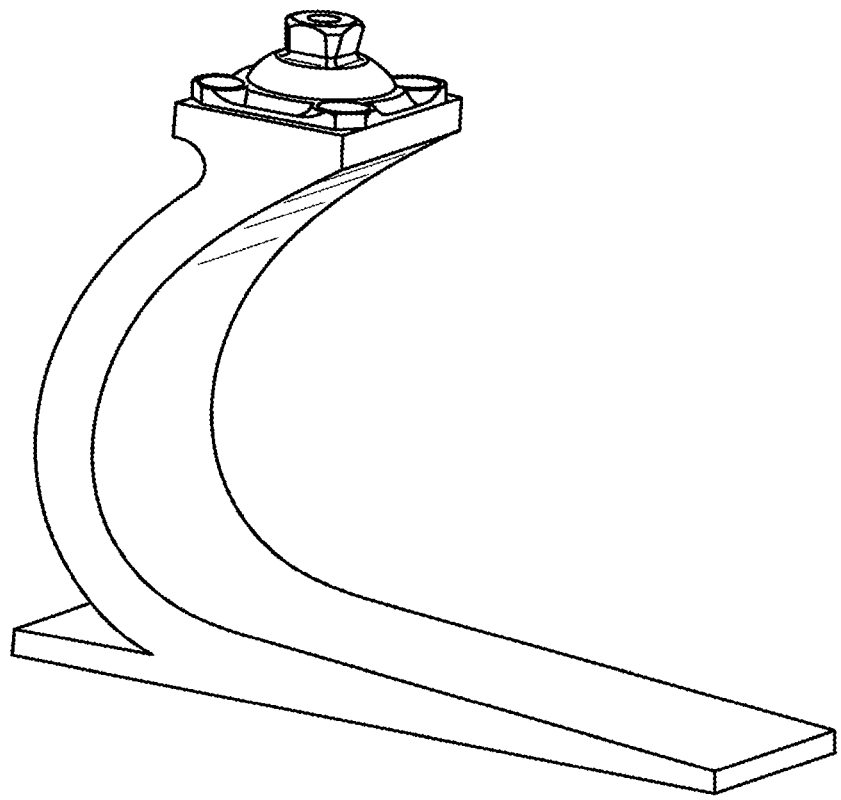
FIG. 12 is a perspective view of one embodiment of a compliant prosthetic foot resulting from one embodiment of a method of the invention.
Figure 13:
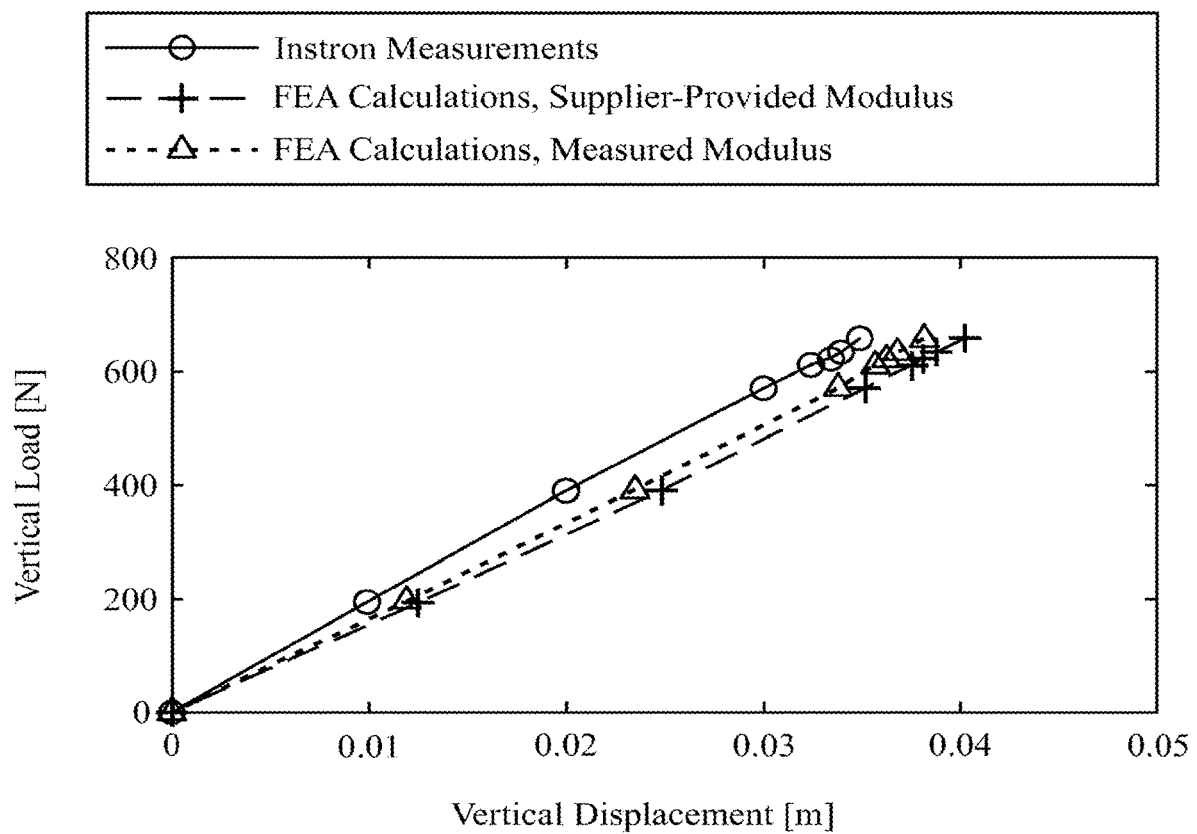
FIG. 13 is a comparison of Instron-measured and FEA-calculated vertical displacements under loads applied at a horizontal distance of 13 cm from the ankle for both the supplier-provided elastic modulus, E=2.41 GPa, and the measured elastic modulus, E=2.54 GPa.

A heel and ankle attachment surface were designed following the method described above (FIG. 12). The foot was machined from nylon 6/6 and weighed 368 g. Using the supplier-provided elastic modulus defined in Section 2.2 of E=2:41 GPa, the FEA solution gave a vertical displacement of 4.0 cm under a vertical load of 658 N applied at a horizontal distance of 13 cm from the ankle, 0.5 cm more than the Instron-measured displacement of 3.5 cm (FIG. 13). The elastic modulus of the material was later measured to be E=2:54 GPa. With this measured modulus, the FEA solution gave a vertical displacement of 3.8 cm under the same vertical load, reducing the difference between the FEA and measured results to 0.3 cm.

Subjects who tested the foot provided mixed feedback. Younger subjects who prioritized mobility over stability liked the foot's energy storage and return compared to the Jaipur foot, which returns very little energy to the user. One subject commented that he could not run with the Jaipur Foot, but could with the prototype. Older subjects and some particularly cautious younger subjects felt unstable on the prototype. Most subjects liked the reduced weight of the prototype relative to the Jaipur Foot, which weighs between 800 g and 1 kg, however one subject commented that because of the lighter weight, he was afraid the foot would break. All subjects commented that they would need a cosmetic cover for the prototype to make it look like a biological foot before they could use it daily. The doctors who run BMVSS and the authors agreed that the negative comments were all either related to the particular subject not being a candidate for an energy storage and return-type foot, which are typically only prescribed to more active subjects, or to the prototype being very different from the Jaipur Foot, which the subjects had been using for a minimum of 10 years and a maximum of 47 years. None of the feedback necessitated significant changes to the design.

A cosmetic cover for the compliant prosthetic formed by the method of the invention can be fabricated to look like a biological foot and to withstand harsh environments, such as barefoot use on rough terrain and submersion in water.

Discussion

The first two optimal designs of the single part keel (green and blue curves in FIG. 11) had smaller LLTE values than any of the simple foot architectures, so they would better replicate the target physiological lower leg trajectory under the five loading scenarios used. When the size of the single part keel was constrained to fit within the envelope of a biological foot, the LLTE value increased to 0.186, approximately equivalent to the simple foot with the rotational ankle and cantilever beam forefoot, and slightly larger than that for the foot with rotational ankle and metatarsal joints. However, the single part keel was the only foot that met the critical requirement of being smaller than a biological foot, which would allow it to fit within a cosmetic and protective cover and be used in shoes. Therefore, this slight decrease in performance is necessary to produce a prosthetic foot for daily use. Additionally, because the wide Bézier curve design does not require multiple parts, such as a spring, axis of rotation, or rigid structural elements, it can be made significantly lighter than either of the articulated simple architectures presented. The method presented here yields a design that is easy to manufacture than the prototypes with articulated ankle joints, as the wide Bézier curve foot consists of a single nylon part that can easily be injection molded or extruded. The genetic algorithm optimization took an average of 15 hours, 1 min and 44 seconds to run. The subsequent pattern search optimization took an additional 1 hour, 38 min and 51 seconds on average. Evaluating the LLTE value for a single design took an average of 6.06 seconds. A framework was developed that uses wide Bézier curve parameterization and a combination of MATLAB scripts and ADINA FEA software to produce a single-part prosthetic foot with a minimal LLTE value.

CONCLUSIONS

The shape and size of a prosthetic foot was optimized as a compliant mechanism with the objective of minimizing the Lower Leg Trajectory Error (LLTE) compared to able bodied values. The forefoot was parameterized as a wide Bézier curve with constraints imposed such that only physically meaningful shapes were considered. The deformed shape of each foot design was calculated for five different loading scenarios representative of different phases of stance using ADINA finite element analysis software, run through a custom MATLAB script. From the deformed shape of the foot, the position of the knee and the orientation of the lower leg segment were found and used to evaluate the LLTE for that particular design. A hybrid of the genetic algorithm and pattern search optimization functions built into the MATLAB optimization toolbox was used to perform the optimization. The final optimal design had an LLTE value similar to previously analyzed articulated prototypes, but unlike these prototypes, the compliant foot fit within the envelope of a biological foot, a critical requirement for a daily-use prosthetic foot. Furthermore, at 368 g, the optimal foot was less than half the weight of the articulated prototypes. The single-part design compliant foot is also far easier to manufacture.

The resulting design was built and tested on an Instron material testing machine to demonstrate that the finite element analysis used to optimize the prosthetic foot indeed matched the physical foot. Under a load of 682 N applied at a horizontal distance of 13 cm from the ankle, the maximum difference between the Instron-measured vertical displacement and finite element results was 0.3 cm, or 9% of the FEA predicted displacement, which is within the expected error of the measurement apparatus. The prosthetic foot was tested qualitatively, and revealed no major design flaws. A cosmetic and protective cover can be built for the foot.

The relevant teachings of all citations, patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:
1. A compliant prosthetic foot, comprising:
a keel; and
a forefoot, a shape of the keel and forefoot defined by a set of determinants for a parametric curve, the determinants iterated to minimize a lower leg trajectory error relative to a target kinematic data set.

2. The compliant prosthetic foot of claim 1, wherein the keel and the forefoot is a singular body.

3. The compliant prosthetic foot of claim 2, wherein the singular body is compliant along its entire length.

4. The compliant prosthetic foot of claim 1, wherein the target kinematic data set includes a physiological data set.

5. The compliant prosthetic foot of claim 1, wherein the set of determinates comprises wide Bezier curve parameters.

6. The compliant prosthetic foot of claim 5, wherein the parametric curve is a cubic curve defined by relative positions of at least two control points.

7. The compliant prosthetic foot of claim 6, wherein the cubic curve is defined by relative positions of at least four control points.

8. The compliant prosthetic foot of claim 5, wherein the set of determinants comprises a width of the Bezier curve as a variable, wherein the width is a function of control circles.

9. The compliant prosthetic foot of claim 8, wherein the width of the Bezier curve is defined as a function of diameters of at least four control circles.

10. The compliant prosthetic foot of claim 1, wherein the set of determinants of the compliant prosthetic foot is set by finite element analysis.

11. The compliant prosthetic foot of claim 10, wherein the finite element analysis is conducted for each of a set time intervals within a gait cycle.

12. The compliant prosthetic foot of claim 11, wherein the time intervals extend from foot flat.

13. The compliant prosthetic foot of claim 12, further comprising a heel component in combination with a wide Bezier curve.

14. The compliant prosthetic foot of claim 13, wherein the time intervals extend from early stance plantar flexion.

15. The compliant prosthetic foot of claim 10, wherein the set of determinants comprises material properties of the keel and forefoot.

16. The compliant prosthetic foot of claim 1, wherein the target kinematic data set is a physiological data set obtained from a subject for whom the compliant prosthetic foot is being fabricated.

17. The compliant prosthetic foot of claim 1, wherein the target kinematic data set is a physiological data set obtained from an able-bodied subject with the same body size and mass as the subject for whom the compliant prosthetic foot is being fabricated.

18. The compliant prosthetic foot of claim 1, wherein the target kinematic data set is a physiological data set scaled from an able-bodied subject to adjust for differences in body size and mass compared to the subject for whom the compliant prosthetic foot is being fabricated.

19. The compliant prosthetic foot of claim 1, wherein the target kinematic data set is obtained by at least one member of the group consisting of: simulation, measurement of a subject, measurement from a population of subjects, and scaling in magnitude from a subject(s) of a different body size and weight.

20. The compliant prosthetic foot of claim 1, wherein the compliant prosthetic foot is fabricated by at least one method selected from the group consisting of: machining; three-dimensional printing; a layup method; a water jet method; additive fabrication; subtractive fabrication; lamination; composite manufacture; injection molding; carbon fiber fabrication; extrusion; casting; molding; co-molding; carving; and vulcanization.

21. The compliant prosthetic foot of claim 1, wherein the compliant prosthetic foot is fabricated of at least one member of the group consisting of: nylon 6/6; carbon fiber; fiber glass; spring steel; titanium; plastic; an alloy of metals; a polymer; a composite; a resin; a thermoplastic; laminate; a rubber; an elastomer; a non-viscoelastic material; a viscoelastic material; and wood.

* * * * *